United States Patent [19]
Chin

[11] Patent Number: 5,922,026
[45] Date of Patent: Jul. 13, 1999

[54] SURGICAL METHOD AND PROSTHETIC STRIP THEREFOR

[75] Inventor: Albert K. Chin, Palo Alto, Calif.

[73] Assignee: Origin Medsystems, Inc., Menlo Park, Calif.

[21] Appl. No.: 08/847,075

[22] Filed: May 1, 1997

[51] Int. Cl.[6] .............................. A61F 2/02; A61B 17/00
[52] U.S. Cl. ........................... 623/11; 606/151; 606/213
[58] Field of Search ............................ 623/11, 12, 13; 606/151, 152, 213

[56] References Cited

U.S. PATENT DOCUMENTS

| | | | |
|---|---|---|---|
| 5,370,650 | 12/1994 | Tovey et al. | 606/151 |
| 5,741,297 | 4/1998 | Simon | 606/151 |
| 5,769,864 | 6/1998 | Kugel | 606/151 |

*Primary Examiner*—David J. Isabella
*Attorney, Agent, or Firm*—Fenwick & West LLP

[57] ABSTRACT

A prosthetic strip or patch and associated surgical procedures allow a surgeon to maneuver the strip or patch without the use of laparoscopic graspers. The prosthetic strip or patch includes pockets into which a fastener tool, used to secure the strip or patch to tissue or to ligaments in the body, is inserted in order to maneuver the strip or patch into selected position and then to tack or otherwise attach the strip or patch to tissue at the selected position.

5 Claims, 4 Drawing Sheets

SURGICAL METHOD AND PROSTHETIC STRIP THEREFOR

BACKGROUND OF THE INVENTION

1. FIELD OF THE INVENTION

This invention relates generally to prosthetic strips for surgery, and, more particularly to a strip or patch having pockets used to suspend prolapsed anatomical structures and repair torn ligaments or tendons.

2. DESCRIPTION OF THE RELATED ART

Prosthetic strips are used in a variety of surgical applications. They may be used to repair torn tendons or ligaments, or they may be used to suspend prolapsed anatomical structures, such as the bladder, vagina, or rectum. To repair torn tendons or ligaments or to suspend prolapsed anatomical structures, a prosthetic strip is used to pull tissue in a desired direction.

Laparoscopic Retropubic Urethropexy ("the LRU procedure") is one application in which prosthetic strips are used. As illustrated in FIG. 1, the LRU procedure involves lifting the bladder neck to alleviate stress urinary incontinence, a symptom often occurring in postpartum women. Specifically, two prosthetic strips are used, one on each side of the bladder. For each prosthetic strip, one end of the prosthetic strip is attached to tissue alongside the bladder neck, and the other end of the prosthetic strip is attached to Cooper's ligament. This pulls upon the bladder neck, thereby changing the angle of the bladder neck relative to the bladder.

According to one known method for performing the LRU procedure, a surgeon inserts an endoscope into the preperitoneal cavity formed by balloon dissection adjacent the bladder, so that the surgeon can view the area in which the procedure is to be performed. The surgeon then places one end of a prosthetic strip on tissue next to the bladder neck. While holding the prosthetic strip in place with a laparoscopic grasper, the surgeon attaches the prosthetic strip to the tissue next to the bladder neck. A fastener tool, such as a tacker or a stapler, is used to attach the prosthetic strip to the tissue. After one end of the prosthetic strip is tacked to the tissue, the other end of the prosthetic strip is positioned on Cooper's ligament and held in place with the laparoscopic graspers while it is tacked to Cooper's ligament with the tacker. This procedure is described in greater detail in the article "Laparoscopic Retropubic Urethropexy," by Stanley L. Hannah, M.D. and Albert Chin, M.D., *The Journal of the American Association of Gynecologic Laparoscopists*, Vol. 4, No. 1, pp. 47–52, the contents of which are fully incorporated by reference herein.

The above described procedure requires a surgeon to make three incisions in the patient. The first incision is to insert the endoscope, the second incision is to insert the laparoscopic graspers, and the third incision is to insert the fastener tool. It is desirable to reduce the amount of incisions made because incisions can leave scars and because post-operative pain increases as the numbers of incisions increase. Therefore, it is desirable to have a prosthetic strip which can be held in place without laparoscopic graspers so that incisions are required only for the endoscope and the tacker.

SUMMARY OF THE INVENTION

The present invention provides a strip or patch, made of bio-inert material, such as polypropylene mesh, for various surgical applications. According to one embodiment, the strip includes two pockets, which are near opposite ends of the strip and are on opposite sides of the strip. The strip may be used to suspend prolapsed anatomical structures or to repair torn ligaments or tendons. A fastener tool, used to tack or staple down the strip, is inserted into one of the pockets to hold the strip in place or to move the strip. Because the pockets allow a fastener tool to maneuver the strip, the need to use laparoscopic graspers to do so is eliminated.

According to an alternate embodiment, a rectangular or square patch of polypropylene mesh has pockets on all four corners of the patch. The patch may be used for hernia repair. A fastener tool, used to tack or staple down the patch, can be inserted into one of the pockets to hold the patch in place or to move the patch.

DETAILED DESCRIPTION OF THE PREFERRED EMBODIMENT

Figure 1:
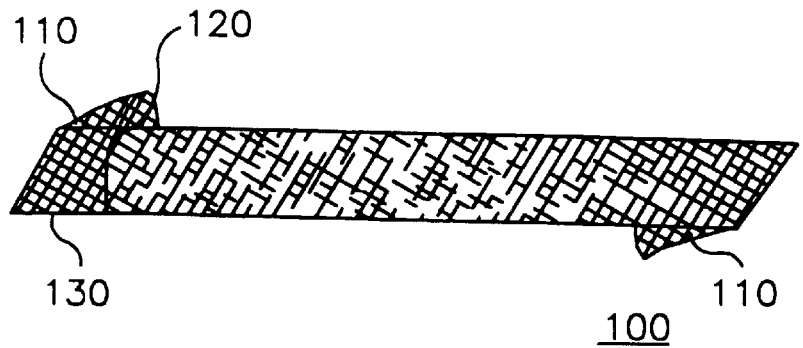
FIG. 1 illustrates a prosthetic strip in accordance with one embodiment of the present invention.

FIG. 1 illustrates a prosthetic strip 100 in accordance with one embodiment of the present invention. For the LRU procedure, the strip 100 is approximately ten centimeters long and one centimeter wide. The strip may be made of polypropylene or polytetrafluoroethylene (PTFE) mesh. The mesh may be a loose, flexible, open, resilient, double knitted weave that is approximately 0.01 to 0.02 inches thick.

In one embodiment, the strip includes two pockets 110 formed near opposite ends and on opposite sides of the strip 100. In an alternate embodiment, the strip includes more pockets 110 on each side of the strip, where the pockets are spaced along the strip 100. The pockets are each approximately 1 centimeter long and 1 centimeter wide, and the opening 120 of the pocket extends approximately 5 to 7 millimeters above the strip 100.

To make the pockets, the ends of the strip 100 are folded over and thermoplastically welded or otherwise suitably attached to the strip 100. In an alternate embodiment, outer edges 130 of the pockets may be sewn to the strip 100.

To illustrate one possible application of the strip 100, use of the strip 100 for the LRU procedure will be described. Note, however, that the strip 100 has many other surgical applications. For instance, it can be used in the repair of torn tendons or ligaments, or it may be used to suspend prolapsed anatomical structures.

To use the strip for the LRU procedure, a 2–3 millimeter diameter probe is inserted into one pocket 110 of the strip 100, and the strip 100 is then inserted, using the probe, into the preperitoneal cavity, located between the bladder and the anterior pelvic wall, through a 5 millimeter trocar port.

Figure 2:
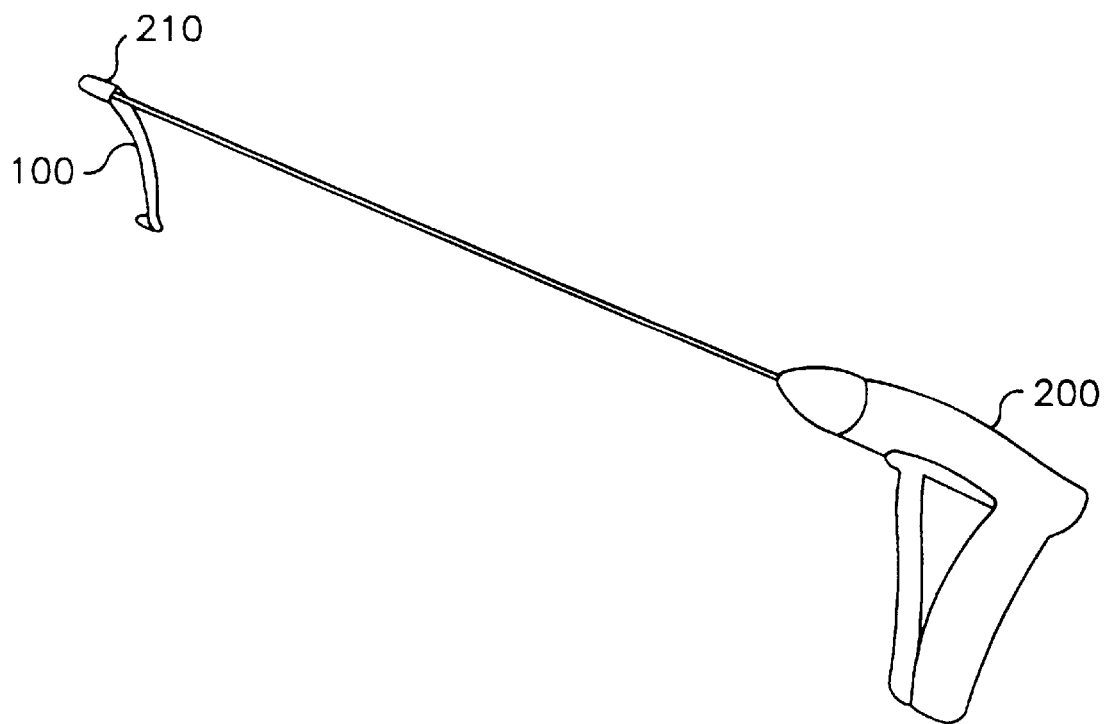
FIG. 2 illustrates a tacker inserted into one pocket of the strip.
Figure 3A:
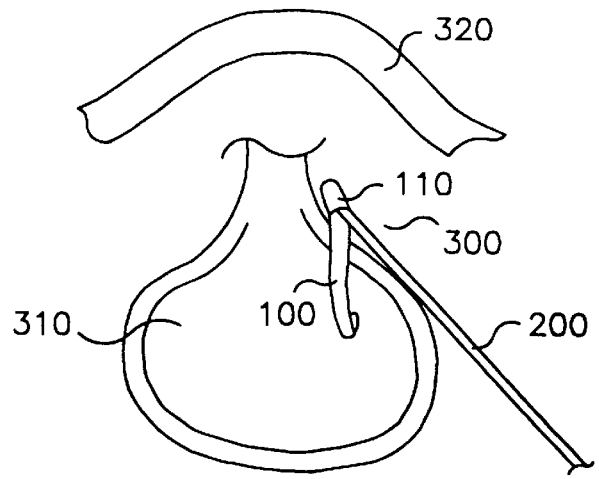
FIG. 3a–3c illustrate the strip being used to suspend a bladder.

The probe is then removed, and a tacker 200, which is illustrated in FIG. 2, is then inserted into the same trocar port. Referring now to FIG. 3a, the tacker 200 is inserted into a pocket 110, which is placed on the periurethral tissue 300 alongside the bladder neck. When the pocket 110 is in the proper position on the periurethral tissue 300, the tacker 200 tacks the pocket 110 down to the periurethral tissue using tacks that may be rotated in a screw-like manner into position or that may be affixed in position in other conventional manners. Since the tacker 200 is used to hold the strip 100 in position, the laparoscopic graspers are not needed, and therefore, only two incisions need to be made on the body.

If the trocar port in which the tacker 200 is inserted is wide enough (about 10 millimeters), it is not necessary to use the 2–3 millimeter diameter probe. This is because the trocar port is then wide enough to fit the tacker 200 and the pocket 110 through the port at the same time. In this case, the tacker 200 is inserted into a pocket 110 of the strip 100, and the strip 100 is inserted into the body using the tacker 200.

Titanium tacks are used to tack the strip 100. The tacker 200 may be the ORIGIN TACKER™ manufactured by Origin Medsystems, Inc. In an alternate embodiment, another type of fastener tool, such as a surgical stapler, may be used instead of the tacker 200. The method of using the strip 100 for the LRU is substantially the same when using a stapler as when using a tacker. Other surgical fastener tools may also be used.

Figure 3B:
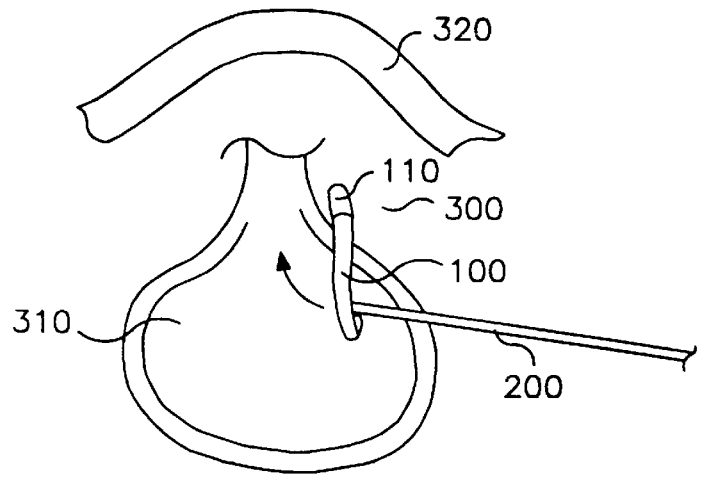

Referring now to FIG. 3b, after one pocket 110 is tacked down, the tacker tip 210 is placed behind the strip 100 (i.e., between the strip 100 and the bladder 310), and, using the tacker 200 to manipulate the strip 100, the strip 100 is flipped over. The tacker tip 210 is then placed in the pocket not tacked down.

Figure 3C:
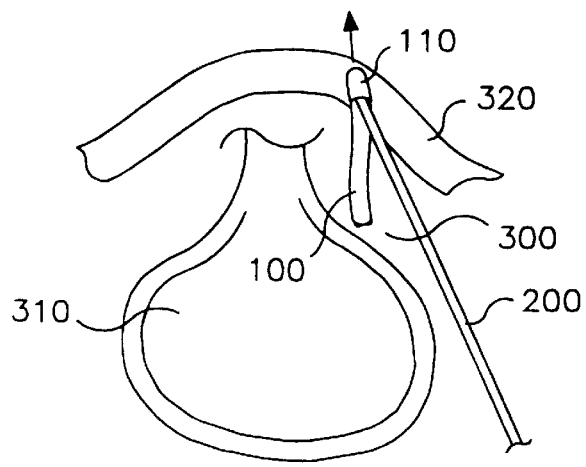

Referring now to FIG. 3c, with the tacker tip 210 in the pocket 110, the end of the strip 100 not tacked down is lifted up to Cooper's ligament 320 by lifting the tacker shaft. The strip 100 is lifted to the extent necessary to achieve the desired amount of bladder neck suspension. Once the strip 100 is lifted up to Cooper's ligament 320, the tacker 200 is used to tack pocket 110 to Cooper's ligament 320. This completes the bladder 310 suspension on one side, and the same procedure is used with another strip 100 on the other side.

Figure 4:
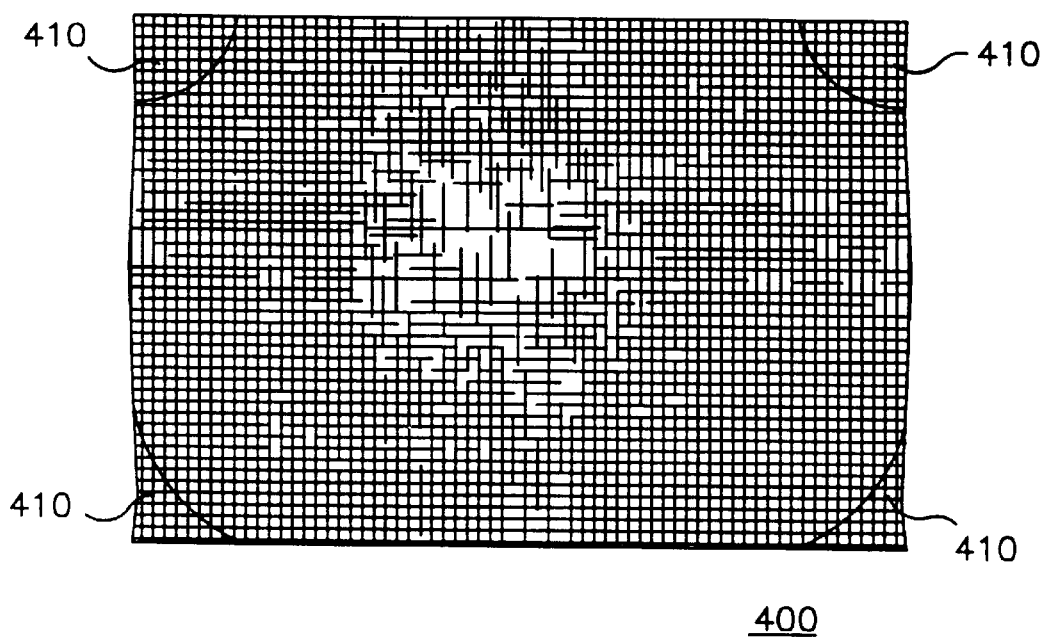
FIG. 4 illustrates a prosthetic patch in accordance with an alternate embodiment of the present invention.
Figure 5A:
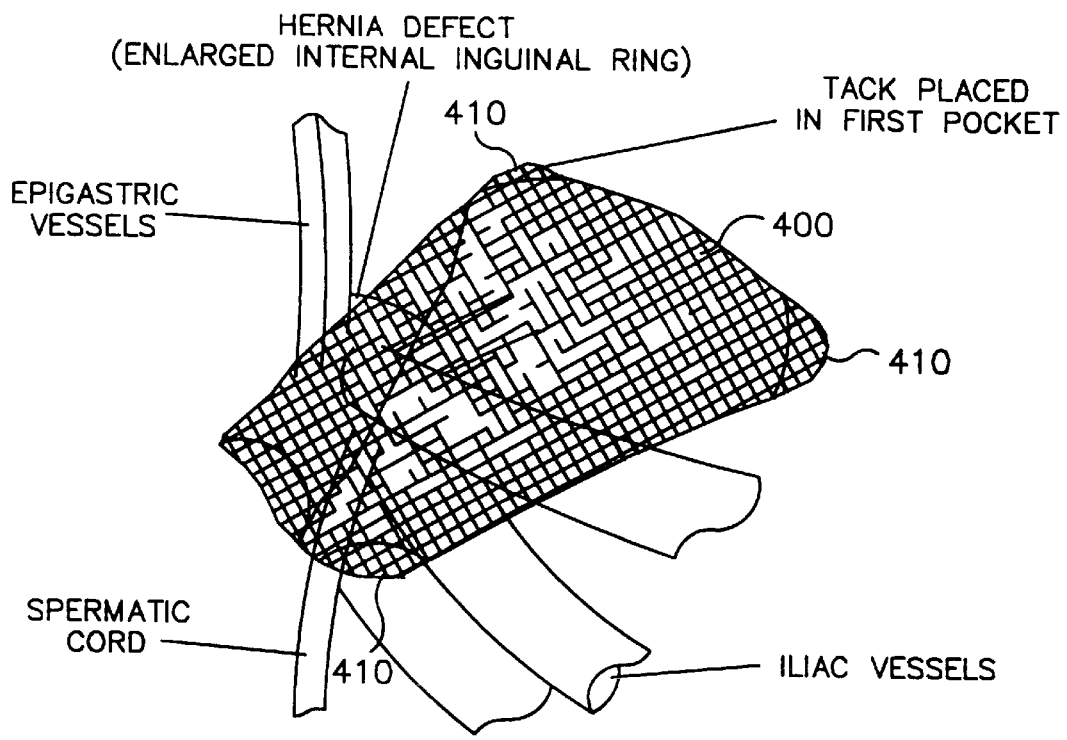
FIG. 5a–5b illustrate the patch being used to repair a hernia.
Figure 5B:
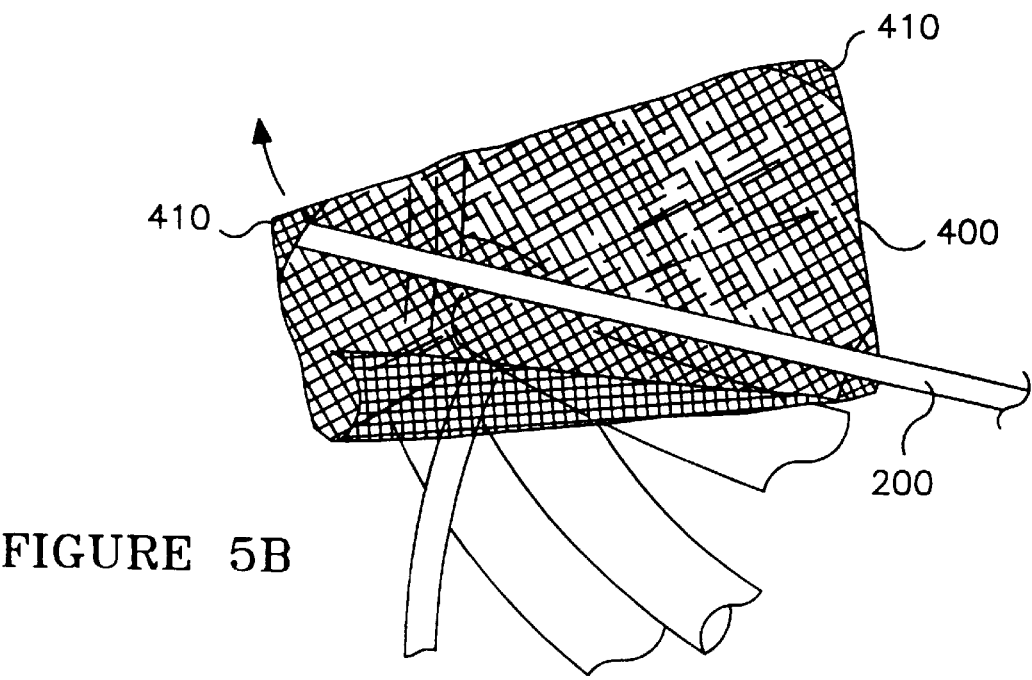

FIG. 4 illustrates an alternate embodiment of the present invention in which pockets 410 are placed on all the corners of a square or rectangular patch 400 of prosthetic mesh. The square or rectangular patch 400 may be used for hernia repair. In one embodiment, the pockets 410 are all placed on the same side of the patch 400, although in other embodiments the number and location of the pockets may vary. A tip of a tacker 200 is inserted into one pocket 410, and, using the tacker 200, the patch 410 is placed in the body, through a 10 millimeter trocar port. As illustrated in FIG. 5a, one pocket 410 is then tacked to the proper tissue. If required, the tacker 200 is used to unroll or straighten the patch 400. As illustrated in FIG. 5b, the tip of the tacker 200 is then inserted into another pocket 410 and is moved to position the patch 400 over the hernia defect. Using the tacker 200, additional tacks are placed to secure the remaining corners. Since the patch 400 can be maneuvered by placing a tacker 200 in a pocket 410, laparoscopic graspers are not needed to perform the procedure, and therefore one less incision need be made.

What is claimed is:

1. A prosthetic strip for use in surgery to repair and/or augment soft tissue, comprising:
    a length of material having at least two ends and two sides; and
    two pockets situated on the material, each pocket located on a different one of the two ends and on a different one of the two sides, and each pocket being of a size and shape to receive a fastener tool.

2. The prosthetic strip according to claim 1, wherein the strip has a plurality of pockets on each one of the two sides of the strip, spaced along the length of the material.

3. The prosthetic strip according to claim 1, wherein the material is polypropylene mesh.

4. A prosthetic patch for use in surgery to repair and/or augment soft tissue comprising:
    a substantially quadrilateral patch of material; and
    four pockets each situated on a different corner of the material and each being of a size and shape to receive a fastener tool.

5. The prosthetic patch according to claim 4, wherein the material is polypropylene.

* * * * *